United States Patent [19]

Pixley

[11] Patent Number: 4,963,657

[45] Date of Patent: Oct. 16, 1990

[54] MONOCLONAL ANTIBODIES TO THE LIGHT CHAIN REGION OF HUMAN FACTOR XII AND METHODS OF PREPARING AND USING THE SAME

[75] Inventor: Robin A. Pixley, Philadelphia, Pa.

[73] Assignee: Temple University of the Commonwealth System of Higher Education, Philadelphia, Pa.

[21] Appl. No.: 204,657

[22] Filed: Jun. 9, 1988

[51] Int. Cl.$^5$ .................... A61K 39/395; C07K 15/28
[52] U.S. Cl. .................................. 530/387; 530/380;
530/382; 530/383; 530/388; 530/413; 530/415;
530/417; 435/240.27; 435/5; 435/7; 424/85.8
[58] Field of Search ............... 530/387, 382, 383, 384,
530/413, 417, 415, 388; 435/240.27, 7.5, 172.2;
424/85.8; 436/548

[56] References Cited

PUBLICATIONS

Akiyama et al., J. Clin. Invest., 78(6), 1631–37, (12/86).
Clarke et al., J. Biol. Chem., 264(19), 11497–502, (7/89).
Campbell, Monoclonal Antibody Technology, chapters 3,4 and 6–10 as supplied, (Elsevier, N.Y.,) 1985.
Saito et al., "Production and Characterization of a Murine Monoclonal Antibody Against a Heavy Chain of Hageman Factor (Factor XII)", Blood 65:1263–1268 (1985).
Small et al., "A Monoclonal Antibody That Inhibits Activation of Human Hageman Factor (Factor XII)" Blood, 65:202–210 (1985).
Laemmle et al., "Enhanced Specificity of Immunoblotting Using Radiolabeled Antigen Overlay: Studies of Bood Coagulation Factor XII and Prekallikrein in Plasma" Anal. Biochem. 156:118–125 (1986).
Laemmle etal., "Quantitative Immunoblotting Assay of Blood Coagulation Factor XII" Thromb. Res. 41:747–759 (1986).
Pixley et al., "A Monoclonal Antibody Recognizing an Icosapeptide Sequence in the Heavy Chain of Human Factor XII Inhibits Surface-Catalyzed Activation" J. Biol. Chem. 262:10140–10145 (1987).
Sugihara et al., "Application of a Monoclonal Antibody Against Factor XII (Hageman Factor); Enzyme-Linked Immunosorbent Assay (ELISA) for Factor XII Antigen", Acta Haematologica Japonica 50:691–5 (May 1987).

Primary Examiner—F. T. Moezie
Assistant Examiner—Jeff Kushan
Attorney, Agent, or Firm—Seidel, Gonda, Lavorgna & Monaco

[57] ABSTRACT

Novel cell lines produce monoclonal antibody to the light chain region of human factor XII. Three such cell lines, ATCC #HB-9703 through ATCC #HB-9704, are formed by fusing SP2/0-Ag14 myeloma cells with spleen cells from BALB/c AnSkh mice immunized with human factor XIIf. Biochemical and therapeutic uses of the monoclonal antibodies are provided.

27 Claims, 4 Drawing Sheets

MONOCLONAL ANTIBODIES TO THE LIGHT CHAIN REGION OF HUMAN FACTOR XII AND METHODS OF PREPARING AND USING THE SAME

REFERENCE TO GOVERNMENT GRANT

The invention described herein was supported in part by National Institutes of Health Grant HL24365. The United States Government has certain rights in the invention.

FIELD OF THE INVENTION

This invention relates to hybrid cell lines for the production of monoclonal antibodies to the light chain region of human factor XII, a protein which is found in nearly all human blood. The invention also relates to the antibody produced by these cell lines, and to therapeutic and biochemical methods using same.

BACKGROUND OF THE INVENTION

Human factor XII is a protein present in blood as a single polypeptide chain in zymogen form. Its concentration in plasma is approximately 29 micrograms/ml. Factor XII is an 80 kDa glycoprotein of beta-globulin mobility composed of 596 amino acids and 16.8% carbohydrate. McMullen et al., J. Biol. Chem. 260:5378 (1985); Fujikawa et al., J. Biol. Chem. 258:10924 (1983). Factor XII participates in the earliest phase of the contact activation system, and is probably the first factor activated during contact activation. It is implicated in mechanisms of inflammation, complement activation, and fibrinolysis. Colman et al., J. Clin. Invest. 73:1249 (1984); Goldsmith et al., J. Clin. Invest. 62:54 (1978).

Human factor XII has been described in the literature as, and is synonymous with, "Hageman factor" and "HF". In vitro activation of factor XII by its physiological activator, kallikrein, results in a cleaved form of factor XII, known as factor XIIa. The latter is composed of two chains, a 50 kDa amino-terminal chain and 28 kDa carboxy-terminal light chain, bonded by disulfide bonds. The factor XIIa light chain contains the enzyme active site or "catalytic triad" of the amino acids serine, aspartic acid and histidine. The factor XIIa heavy chain contains the surface binding domain. Human factor XIIa has been described in the literature as, and is synonymous with, "activated Hageman factor", "alpha-factor XIIa", "HFa" and "factor XIIa HMW".

Factor XII fragment (XIIf), a 32 kDa further cleavage product of factor XIIa, is composed of the 28 kDa light chain bonded through disulfide bridges to a 2–4 kDa carboxyl-terminal fragment of the heavy chain. Factor XIIf has been described in the literature as, and is synonymous with, "factor XII fragment", "beta-factor XIIa", "HFf" and "factor XIIa LMW".

Other cleaved forms of factor XII, produced by kallikrein, trypsin, plasmin, and autoactivation have been described in the literature. Dunn et al., J. Biol. Chem. 257:1779 (1982); Margolis, J. Physiol. (Lond.) 144:1 (1958); Kaplan et al., J. Exp. Med. 133:696 (1971).

In vitro activation of factor XII to the active enzyme factor XIIa occurs on negatively charged surfaces by autoactivation, by proteolytic cleavage, by conformational change, or by some combination of these mechanisms. Non-physiological substances with negatively charged factor XII-activating surfaces include glass, kaolin, celite, dextran sulfate, ellagic acid, sulfatides and cholesterol sulfates. Biological substances that activate factor XII include chondroitin sulfate, heparin and some mast cell proteoglycans. Hojima et al., Blood 63:1453 (1984).

Activation of the contact system through activation of factor XII leads to coagulation, and the release of bradykinin. According to one reaction, surface-bound factor XIIa forms an enzyme-substrate complex with factor XI and catalyzes the conversion of factor XI to its active form, factor XIa. Factor XI is a 160 kDa proenzyme consisting of two identical disulfide-linked polypeptide chains. Factor XI is associated in plasma with the 120 kDa protein high molecular weight kininogen ("HMWK") in a stoichiometric noncovalent complex. HMWK serves as a nonenzymatic cofactor in the factor XIIa-catalyzed conversion of factor XI to factor XIa. Factor XIa in turn activates factor IX, which leads to the sequential activation of the remainder of the coagulation cascade.

According to another reaction, surface-bound factor XIIa cleaves and activates prekallikrein to the active enzyme kallikrein. Prekallikrein is an 88 kDa proenzyme complexed with HMWK. Kallikrein cleaves HMWK to liberate bradykinin, the most potent vasodepressor peptide known. Kallikrein may also cleave factor XIIa once again, forming factor XIIf, which can diffuse back into solution. Kallikrein is also able to dissociate from the activator surface and diffuse into solution to activate more factor XII elsewhere on the surface. Colman et al., J. Clin. Invest. 73:1249 (1984).

While both factor XIIa and factor XIIf activate factor XI, factor XIIa is much more effective, presumably due to some structure on the factor XIIa heavy chain. However, both factor XIIa and factor XIIf are equally potent in the conversion of prekallikrein to kallikrein.

Gram negative septicemia is a major cause of death and disability among hospitalized patients, with an incidence of several hundred thousand individuals effected each year. Once hypotension occurs in association with circulating bacteria or bacterial endotoxin, the mortality ranges from 40–60%. Another frequent complication is hemorrhage due to disseminated intravascular coagulation. Colman et al., Annu. Rev. Med. 30:359 (1979). The microvascular thrombosis which characterizes this condition leads to consumption of coagulation proteins and platelets, and bleeding due to inadequate hemostasis. Id.

Both the hypotension and the hemorrhage experienced in gram negative septicemia patients is due to activation of the contact activation system by bacteria or its endotoxins. The endotoxins causes activation of factor XII. The active enzyme factor XIIa, in turn acts on its two substrates, factor XI and prekallikrein, resulting in coagulation and bradykinin formation.

Clinical and experimental evidence has indicated that kallikrein activation, and the resulting generation of bradykinin, is responsible for the early phase of hypotension experienced by gram negative septicemia patients. The clinical result of the activation of factor XIIa-induced activation of factor IX, which leads to the sequential activation of the remainder of the coagulation cascade, is disseminated intravascular coagulation with sequela, hemorrhage and/or thrombosis.

At present, the treatment of hypotensive septicemia is difficult due to the danger of volume overload and increased hemorrhage due to heparin treatment of disseminated intravascular coagulation. Since there can be a 50% mortality in this condition in the first 48-hours, new approaches to treatment are needed. What is needed is a specific inhibitor of factor XIIa to control the activation of the contact system and release of bradykinin observed in gram negative septicemia patients.

In a related problem, clinical evidence suggests that side reactions occur in some commercially-prepared blood products due to the presence of an activated factor XII derivative. A fraction of human plasma containing factor VIII prepared by ether fractionation in glass bottles has been observed to give rise to prominent flushing and hypotension in patients, resembling the response to injection of bradykinin, which is a by-product of factor XII activation. Arterial hypotension has been reported to occur in patients given such preparations. Reactions to albumin substitutes have been shown to be due to the presence of factor XIIf in such products. Moreover, the presence of factor XIIf in vivo will cause an immediate 50% drop in blood pressure. Thus, its presence in blood products must be avoided. What is needed is an efficient means for purifying liquids, such as blood products, by removing factor XIIf and related activated factor XII derivatives which may be presented in the liquid.

Kohler and Milstein, Nature 254: 493–497 (1975) were the first to describe the fusion of myeloma cells to immune spleen cells from mice to generate continuous cell lines. These hybrid cell lines, or hybridomas, have characteristics that neither the parental myeloma cells nor parental immune spleen cell possess. Hybridomas are capable of continuously producing homogeneous (monoclonal) antibodies. Prior to the work of Kohler and Milstein, only polyclonal antisera could be obtained.

Although techniques for the production of hybridomas are now extensively described in the literature, e.g., *Monoclonal Antibodies, Hybridomas: A New Dimension In Biological Analysis*, R. H. Kennet, T. J. McKearn, and K. B. Bechtol, eds., Plenum Press, New York and London (1980), there is no general method for obtaining successful monoclonal antibody-producing hybridomas which can be used with all antigens. Fusion techniques must be varied in each case to obtain hybridomas producing monoclonal antibody to the desired antigen. In order to obtain antibodies specific to a single antigen, laborious purification techniques are required to provide highly purified antigen for immunization. The production of monoclonal antibodies for any given antigen is still a highly empirical process.

Monoclonal antibodies to factor XII directed to an epitope within the heavy chain region of the molecule have been reported. Small et al., Blood 65:202 (1985); Saito et al., Blood 65:1263 (1985); Pixley et al., J. Biol. Chem. 262:10140 (1987). However, because the light chain contains the active enzyme site responsible for catalyzing the cleavage of prekallikrein to kallikrein, and the activation of factor XI to factor XIa, monoclonal antibodies to the heavy chain can at best only partially block these enzyme activities.

Polyclonal antibodies to human factor XII have been reported. Lammle et al., Anal. Biochem. 156:118–125 (1986); Lammle et al., Thromb. Res. 41:747–759 (1986). Such antibodies, being polyclonal, are not specific for a single antigenic determinant.

As used herein, "factor XII light chain" or "light chain region of factor XII" shall mean the 28 kDa carboxy-terminal portion of human factor XII which contains the active enzyme site, without regard to whether said portion is in free form or is covalently linked to other peptide chains, as in factor XII, XIIa and XIIf. Similarly, as used herein, "immunogen containing factor XII light chain" shall include factor XII, factor XIIa, factor XIIf, and other cleaved forms of human factor XII containing the 28 kDa light chain, and shall also include the 28 kDa light chain itself.

As used herein, the expression "monoclonal antibody" (occasionally abbreviated "Mab") shall include not only the intact antibody, but also fragments thereof capable of binding antigen, including, but not necessarily limited to Fab and F(ab')$_2$ fragments.

As used herein, the expression "blood plasma product" means human plasma or fractions of human plasma, such as fractions containing one or more specific proteins, or purified preparations of such plasma proteins.

SUMMARY OF THE INVENTION

According to the present invention, novel hybridomas have been prepared providing cell lines producing monoclonal antibodies which specifically bind to an antigenic determinant in the light chain region of human factor XII. Each hybridoma comprises a cell hybrid formed by fusion of cells from a myeloma line and spleen cells from a donor previously immunized with an immunogen containing human factor XII light chain. Illustrative hybridomas include, ATCC #HB-9703, ATCC #HB-9704 and ATCC #HB-9705. Each antibody so produced is specific for an antigenic determinant of the light chain region of human factor XII. The purified monoclonal antibody contains essentially no other anti-human protein immunoglobulin. The hybridomas may be cultured in vitro to secrete antibodies.

The hybrid cell lines of the present invention may be prepared by first immunizing a splenocyte donor with an immunogen containing human factor XII light chain. Purified human factor XIIf is the preferred immunogen. The spleen cells are fused with myeloma cells in the presence of a fusion promotor. The fused cells are diluted and cultured in separate wells in a medium which will not support the unfused myeloma cells. The supernatant in each well is assayed for the presence of antibody to human factor XIIf by an assay such as an enzyme-linked immunosorbent assay ("ELISA"). Hybridomas secreting antibody which bind to human factor XIIf are selected and cloned.

The hybridomas are cultured in a suitable medium and the antibody is recovered from the supernatant. Alternatively, the clones are transferred intraperitoneally into mice, and the resulting malignant ascites and serum containing the desired antibody are harvested.

A method for removing human factor XII and factor XII fragments containing the factor XII light chain from liquids is also provided. An immobilized monoclonal antibody which binds to an antigenic determinant in the light chain region of human factor XII is contacted with the liquid. Factor XII and fragments thereof containing the light chain are absorbed therefrom. Blood products may be advantageously purified of factor XII and factor XII light chain-containing fragments in this manner.

It is accordingly an object of the invention to provide hybridomas which produce antibodies against the light chain region of human factor XII.

It is another object of the invention to provide essentially homogeneous antibodies against human factor XII light chain.

It is another object of the invention to provide a method for removing human factor XII and active fragments thereof from liquids, such as blood plasma products.

It is an object of the invention to provide a method for determining the level of factor XII in specimens of interest.

It is yet another object of the invention to provide a therapeutic method for inhibiting the activity of human factor XIIa or factor XIIf in vivo in human disease states.

The subject hybridomas are identified herein by the same number assigned to the antibody produced thereby. Thus, for example, the designation "B6F5" pertains to both the hybridoma 1H9B6F5 and the monoclonal antibody produced by this hybridoma. The particular material referred to, that is, hybridoma versus antibody, is apparent from the context.

The subject hybridomas were deposited on April 28, 1988 in the American Type Culture Collection, 12301 Parklawn Drive, Rockville, Md. 20852, and were given the following ATCC accession numbers: #HB-9703 for 1B2D2E10; #HB-9704 for 5G3C6B7; and #HB-9705 for 1H9B6F5.

DETAILED DESCRIPTION OF THE INVENTION

Figure 1:
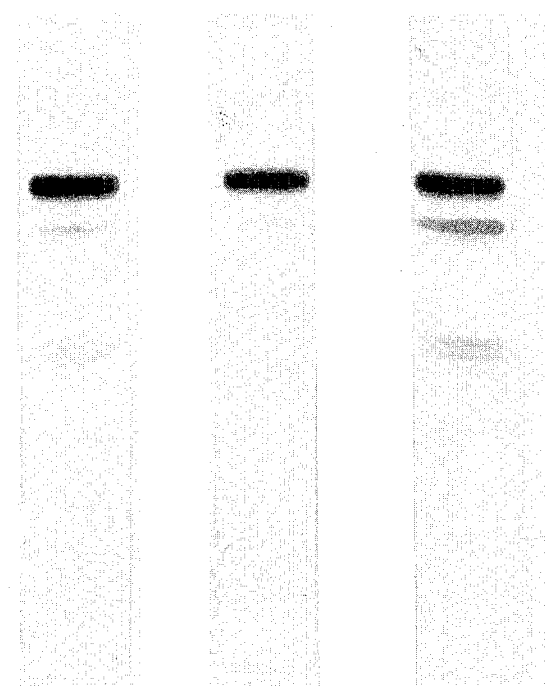
FIG. 1 is a photograph of a Western Blot/ELISA of kallikrein-cleaved factor XII fragments indicating that each light chain antibody (B6F5, C6B7, D2E10) reacts with factor XIIf (30 kDa) as well as with zymogen factor XII (80 kDa) and other fractions containing the light chain region.

The cell hybrids of the present invention produce monoclonal antibodies that react with human factors XII, XIIa and XIIf, all of which contain the light chain region of factor XII. The epitope recognized by the antibodies is thus located within the light chain region of factor XII. The antibodies significantly inhibit the coagulant activity of human factor XII, and significantly inhibit the amidolytic activity of factor XIIf. These findings indicate that the epitope is located within the light chain region of factor XII. Light chain specificity is further supported by the fact that the antibodies significantly inhibit the activation of prekallikrein by factor XIIf, indicating blockage of the light chain region of factor XII from acting on one of its natural substrates.

The monoclonal antibodies of the invention are specific to human antigen, and do not inhibit factor XII coagulation activity in plasma of rat, mouse, pig, rabbit or hamster.

The three monoclonal antibodies prepared are from subclass IgG$_1$, and contain the kappa light chain. The purified antibodies have an apparent molecular weight on non-reduced 12% sodium dodecyl sulfate polyacrylamide gels of 200 kDa which, upon reduction with dithiothreitol, yields 50 kDa and 28 kDa fragments.

The monoclonal antibodies of the invention are prepared by immunizing an appropriate host with factor XIIf. The immunogen may be isolated from surface-activated or kallikrein-activated purified factor XII by ion exchange chromatography techniques. Pixley et al., Arch. Biochem. Biophys. 256:490 (1987). Alternatively, factor XIIf may be isolated directly from plasma by the ion exchange technique described by Tankersley et al., Thromb. Res. 25:307 (1982). Other purification methods may be used, including binding with immobilized monoclonal antibody according to the present invention.

According to one method, mice are immunized with purified factor XIIf. BALB/c AnSkh mice are preferred, although other strains may be used. The immunization schedule and concentration of immunogen administered should be such so as to produce useful quantities of suitably primed splenocytes.

Upon completion of the immunization regimen, more fully described below, the mice are sacrificed and their spleens removed. A suspension of splenocytes in a suitable medium is prepared. Approximately 2.5–5 ml of medium per spleen is sufficient. The protocols for in vitro cell suspension are well established.

The spleen cells are fused with mouse myeloma cells by means of a fusion promoter. The preferred fusion promoter is polyethylene glycol ("PEG"), molecular weight 1,300–1,600 kDa. Other fusion promoters may be used. The mouse myeloma cell line is preferably one of the "drug-resistant" types, to enable selection of hybrids. The most frequently used class of myelomas are the 88-azaguanine-resistant cell lines, which are widely known and available. These cell lines lack the enzyme hypoxanthine guanine phosphoribosyl transferase and therefore do not survive in "HAT" (hypoxanthine-aminopterinthymidine) medium. The use of myeloma cells with different genetic deficiencies (e.g., other enzyme deficiencies, drug sensitivities, etc.) that can be selected against in a medium supporting the growth of genotypically competent hybrids is also possible. Additionally, it is suggested that the myeloma cell line should not itself produce any antibody, although in some circumstances secreting myeloma cell lines may be used.

While the preferred fusion promoter is PEG of average molecular weight 1,300–1,600 kDa (available from ATCC), other known fusion promoters may be used.

Fusion of cells may be carried out in an adherent monolayer, such as according to the method described by T. J. McKearn, "Fusion of Cells in an Adherent Monolayer" in *Monoclonal Antibodies: Hybridomas: A New Dimension In Biological Analysis*, (Kennett, R. H., McKearn, T. J., and Bechtol, K. B., eds., Plenum Press, New York and London, 368–369, 1980). Other fusion techniques may be employed. A cell ratio of 2–5:1 spleen cells per myeloma cell may be used. This ratio may be varied depending on the source of spleen or myeloma cells.

A mixture of unfused myeloma cells, unfused spleen cells and fused cells are distributed for culturing in separate compartments (e.g., the wells of microtiter plates) in a selective medium in which the infused myeloma cells will not service. Distribution of the cells may be by resuspension in a volume of diluent which is statistically calculated to isolate a desired number of cells per compartment. *See*, McKearn, T. J., "Cloning of Hybridoma Cell Lines by Limiting Dilution in Fluid Phase" in *Monoclonal Antibodies*, p. 374.

When HAT is used as the medium, unfused 8-azaguanine-resistant myeloma cells will not grow. Unfused spleen cells will normally die after a few days, since they are non-malignant. Culturing proceeds for a time sufficient to allow their death. Fused cells continue to reproduce and grow in the selective medium.

The supernatant in each container or compartment having hybrid cell growth is screened and evaluated for the presence of antibody to factor XIIf. Any suitable antibody-binding detection method may be used, e.g., ELISA, radioimmunoassay, etc.

After selection and cloning, monoclonal antibody to the factor XII light chain region may be produced by in vitro culturing of the hybridomas or by in vivo peritoneal exudate induction in mice. The first method will yield monoclonal antibody of higher purity. The antibody is recovered from the supernatant essentially free of undesired immunoglobulin. Antibody concentrations of 25–50 micrograms/ml are possible by this method. In growth media containing serum (such as fetal calf serum) a small amount of other immunoglobulin is present.

Where concentrations of antibody larger than those obtained by in vitro culturing of hybridomas are required, the subject hybridomas may be injected into the peritoneal cavity of syngeneic or semisyngeneic mice. After a suitable period of incubation, the hybridomas cause formation of antibody-secreting tumors, which will produce 4–10 mg of antibody per ml of peritoneal exudate of the injected mouse. Since mice have normal antibodies in their blood and ascites, a contamination of about 5% from the host mouse is inevitable. Purification of ascites monoclonal antibody may remove these contaminants. The resultant antibody is of high titer, being active at dilutions of 1:300,000 or higher.

The following is one typical procedure for preparing cell lines according to the present invention, which is not intended to be limited to the same.

I. PREPARATION OF THE IMMUNOGEN

Factor XIIf was isolated from an activated mixture of purified factor XII as follows.

Plastic containers and columns are used throughout the purification procedure. All dialysis tubing and plastic containers are prerinsed with 2 mg/ml of polybrene in $H_2O$, then rinsed with $H_2O$. All steps are carried out at room temperature except where indicated. Concentration of factor XII is performed by negative pressure dialysis at 4° C.

A. Preparation of Purified Factor XII

Purified factor XII may be prepared according to the following procedure of Pixley R. A. and Colman, R. W., Thromb. Res. 41:89 (1986). The method relies on the ability of factor XII to preferentially bind to a zinc-chelate affinity resin.

Fresh frozen plasma (4005 ml) containing 4% sodium citrate as anticoagulant was quickly thawed in a polypropylene container at 37° C. containing soybean trypsin inhibitor ("SBTI") (0.1 mg/ml) and polybrene (0.36 mg/ml), and treated as follows:

Ammonium Sulfate Precipitation. 25–50%: Crystalline ammonium sulfate (144 gm/L plasma) was slowly dissolved in the plasma and stirred for 30 minutes. The solution was centrifuged at 13,680 x g, for 30 minutes. Ammonium sulfate (158 gm/L) was slowly dissolved in the decanted supernatant at room temperature and stirred for 60 minutes. The precipitate was dissolved in minimal amounts (1 liter) of 0.025M $Na_2HPO_4$, 0.8M NaCl, 0.2 mg/ml SBTI, 0.36 mg/ml polybrene, 0.02% $NaN_3$, pH 6.5, and dialyzed overnight against two changes of 20 liters of the same buffer without SBTI at 4° C.

Zinc Chelate Chromatography #1: The dialyzed solution was centrifuged for 10 minutes at 4000 x g to remove precipitate formed during dialysis. Three hundred ml of equilibrated Zinc Chelate Sepharose was placed in a plastic Buchner funnel under low vacuum. The solution was slowly allowed to flow through the resin and was collected. The resin was washed with equilibrating buffer and collected in 500 ml fractions until the absorbance readings at 280 nm were below 0.1 (approximately 11 liters). The resin was then washed with 2 to 3 liters cacodylate buffer (0.02M Na cacodylate, 0.15M NaCl, 0.1 mg/ml SBTI, 0.03 mg/ml 35 polybrene, 0.02% $NaN_3$, pH 5.5) until the absorbance readings of the fractions were below 0.1. Factor XII fractions were eluted with 10 liters of acetate buffer (0.1 M sodium acetate, 0.8M NaCl, 0.1 mg/ml SBTI, 0.03 mg/ml polybrene, 0.02% $NaN_3$, pH 4.5). The fractions were assayed for factor XII coagulant activity. The factor XII fractions were pooled and dialyzed overnight against two changes of 20 liters of phosphate-acetate buffer (0.25M $Na_2HPO_4$, 0.005M sodium acetate, 0.8M NaCl, 0.001 mg/ml polybrene, 0.02% $NaN_3$, pH 6.5) at 4° C.

Zinc Chelate Chromatography #2: The dialyzed factor XII fractions were applied to a column (2.5×25 cm) containing 120 ml of phosphate-acetate-buffer-equilibrated Zinc Chelate Sepharose and washed overnight with 2 liters of the same buffer at a flow rate of 100 ml/hr. A pH gradient of 250 ml each of the phosphate-acetate buffer at pH 6.5 and 4.0, followed by a 100 ml wash of pH 4.0 buffer, was applied to the column and 5 ml fractions were collected. Five hundred microliter aliquots were placed in polypropylene Eppendorf tubes for analysis and the fractions and aliquots were frozen at −70° C. The gradient aliquots are analyzed for protein, factor XII coagulant activity, and S-2302 amidolytic activity, and were also subjected to sodium dodecyl sulfate polyacrylamide gel electrophoresis ("SDS-PAGE"). The fractions determined to contain factor XII were pooled and concentrated in portions by negative pressure dialysis against Phosphate-acetate buffer, pH 6.5.

Gel Filtration: Aliquots containing 50-100 units of factor XII coagulant activity were applied to a 1.5×88 cm column of Biogel A 0.5 equilibrated with phosphate-acetate buffer at a flow rate of 1 ml/min. Two ml fractions were collected and analyzed for protein, coagulant activity, and S-2303 amidolytic activity, and subjected to SDS-PAGE. The 2 ml fractions were frozen. The fractions determined to contain purified factor XII were thawed and concentrated by negative pressure dialysis against Phosphate-acetate buffer.

B. Conversion of Factor XII to Factor XIIf

Factor XII was converted to factor XIIf in a manner similar to that described in Silverberg et al., J. Biol. Chem. 225:7281 (1980), and reported in Pixley et al., J. Biol. Chem. 260:1723 (1985). According to this method kallikrein (0.4 micromoles) was incubated with purified factor XII (2.2 micromoles) in a buffer (0.02M Tris, 0.02M NaCl, 0.1% PEG 8000, pH 7.5) at 37° C. for 40-60 minutes in a polypropylene test tube. Kallikrein was separated from factor XII, factor XIIa and factor XIIf on a small QAE sepharose column (2 ml) equilibrated with the incubation buffer. Kallikrein was completely removed by elution with 0.1M NaCl in this buffer. Factor XII, factor XIIa and factor XIIf were consecutively eluted with a 24 ml gradient of 0.1-0.6M NaCl. Each 1 ml fraction was characterized by SDS-PAGE, clotting activity and amidolytic activity with the substrate S-2302 to determine the characteristics of the proteins present. Samples were frozen at −30° C. until used.

While the above method of immunogen preparation employs a zinc-chelate chromatographic method for obtaining purified factor XII, other methods of isolating factor XII may be used. An alternative isolation procedure consists of ammonium sulfate precipitation and ion exchange chromatography under different pH and ionic strength conditions. Yet another technique for isolating factor XII uses monoclonal antibody to factor XII heavy chain in an immunoaffinity purification method. Pixley et al., J. Biol. Chem. 262: 10140 (1987). Any of the methods hereinmentioned provides a purified, functionally active factor XII product which may be converted to factor XIIf to serve as the immunogen in the practice of the present invention.

II. IMMUNIZATION

Four male or female BALB/c AnSkh mice, 8-10 weeks old were immunized subcutaneously with 35 micrograms of protein/mouse in complete Freund's adjuvant (week 0) and then again subcutaneously with 35 micrograms of protein/mouse in incomplete Freund's adjuvant at week 5. Blood was removed and screened at week 7 for antibodies to the immunogen using ELISA. At week 11, 50 micrograms of immunogen/mouse in 0.15M NaCl were intraperitoneally injected. Four days later, blood was removed from the retro-orbital plexus of each mouse under light anesthesia, and the two strongest positive mice were selected as spleen donors. The spleens of these animals were asceptically removed and placed in tissue cultured dishes (15×60 mm) containing Hank's balanced salt solution ("HBSS", Gibco, Grand Island, N.Y.) to which 50 micrograms/ml of gentamycin or "PEN/STREP" (Gibco) were added. The latter is a mixture of penicillin and streptomycin. The spleens were then transferred into other culture dishes containing HBSS. The spleens were teased apart with sterile forceps and then transferred into a centrifuge tube which was placed in ice for two minutes to allow large debris to settle. The cell-suspension was transferred into another centrifuge tube and spun for ten minutes at 1200 rpm. After discarding the supernatant, the cells were resuspended in 5-10 ml of 0.17 M $NH_4Cl$ (ice cold) and placed in ice for five minutes with occasional mixing in order to lyse red blood cells. The cell suspension was gently underlaid into 10 ml of a 1:1 dilution of HBSS:normal serum and centrifuged at 1200 rpm for ten minutes. Fetal calf serum ("FCS") may be used as the normal serum. The cells were then washed thrice in Dulbeco's Modified Eagle's Medium ("DME", Gibco). The number and viability of cells were then determined.

SP2/O-Ag14 myeloma cells used in the hybridization procedure were washed in the same way as the unlysed splenocytes.

III. PREPARATION OF SPLENOCYTE FEEDER LAYERS

On the day of fusion, non-immune splenocytes from the same mouse strain as immunized above were processed according to the same procedure without immunization and without washing in DME. These non-immune splenocytes were used to prepare feeder layers as follows. The non-immune cells were resuspended in DME+HAT+20% FCS to a density of $2-4\times10^6$ cells/ml. These cells were seeded onto 96-well plates ($1-2\times10^5$ cells/well) and incubated in 5% $CO_2$ at 35° C. overnight as a sterility check before plating out hybrid cells.

IV. HYBRIDIZATION

Fusion was carried out as follows. 1.5 ml of immune splenocytes and 1.5 ml of SP2/O-Ag14 cells were pipeted onto a concanavalin A-coated plate. The cell concentration of each cell type was adjusted so that the ratio of splenocytes to SP2/O-Ag14 cells was 2-3:1, with a total of $7-10\times10^7$ cells/plate. The plates were then incubated in 5% $CO_2$ at 37° C. for 45-60 minutes to allow for attachment of the cells to concanavalin A. Fusion was performed by adding 1 ml of a 50% DME:-PEG solution to each plate, drop by drop. The plates were left standing for 15 seconds after the addition of the first drop. The cells were then washed twice with 5 ml of DME. Following addition of 5 ml of DME+20% FCS/plate, the cells were incubated overnight.

V. SELECTION AND GROWTH OF HYBRIDOMAS

Following overnight incubation, the cells from the above hybridization procedure were transferred into centrifuge tubes and spun at 1500 rpm for 15 minutes. The supernatants were discarded. The cells from each tube were suspended in 40-45 ml of DME+HAT+20% FCS and transferred into the 96-well plates (0.1 ml cell suspension/well) containing non-immune splenocyte feeder layers as prepared in "III. Preparation of Splenocyte Feeder Layers", above. The plates were cultured with 10% $CO_2$ at 37° C. in a humid atmosphere. The cells were allowed to grow for 3-5 days, after which an additional 0.1 ml of DME+HAT+20% FCS were added to each well. Hybrids were checked daily. Three to four weeks after fusion, the cells were switched to DME+HAT+10% FCS (no aminopterin). Hybridoma cultures with antibody reactive to the immunogen were selected and cloned and subcloned by a limiting dilution technique. (McKearn, T. J. "Cloning of Hybridoma Cells by Limiting Dilution and Fluid Phase" in *Monoclonal Antibodies.* p. 347). Cells from the three strongest antigen-position subcloned cultures as determined by ELISA screening (i.e., 5G3C6B7, 1H9B6F5, and IB2D2E10) were selected and injected intraperitoneally (about $2\times10^6$ cells in 0.5 ml PBS/mouse) into four BALB/c mice which had been primed 10–14 days previously with 0.5 ml of pristane (2, 6, 10, 14-tetramethylpentadecane). After 7–14 days, the blood was removed from the retro-orbital plexus of each mouse, under light ether anesthesia, and the tumor-induced ascites fluid was harvested.

VI. PURIFICATION OF THE MONOCLONAL ANTIBODIES

Antibody from ascites fluid prepared above may be purified by Protein-A affinity chromatography using a commercially available kit (Affi-Gel Protein-A, Bio Rad Corp., Richmond, Calif.). Ascites fluid is diluted 1:1 in a binding buffer. The crude material is applied onto the Protein-A column, and the column is washed with binding buffer such that the absorbance at 280 nm is less than 0.025. The antibody is then eluted with an acidic buffer. The peak of elution is pH neutralized, pooled, concentrated and dialyzed against 0.02M Tris, 0.15M NaCl, 0.03% sodium azide, pH 7.5. The concentration of the antibody is determined by reading the absorbance at 280 nm and calculating the mg/ml by using a 1% extinction coefficient of 14.2. The final antibody concentration is in the range of 2–5 mg/ml. Concentrations of the monoclonal antibodies may be converted from mg/ml to micromolar using an antibody molecular weight of 150 kDa.

VII. CHARACTERIZATION OF THE MONOCLONAL ANTIBODIES

The sub-class of the monoclonal antibodies was determined with a mouse immunoglobulin subtype identification kit (Mannheim Boehringer). MAbs B6F5, C6B7, and D2E10 were all identified as sub-class $IgG_1$, kappa light chain. The quality of the final antibody preparation was determined by SDS-PAGE according to a modified procedure of Laemmli, Nature 227:680 (1970). All the monoclonal antibodies under non-reducing condition were observed to be single bands of approximately 200 kDa. Upon reduction, the purified antibodies resulted in a band at 50 kDa and 28 kDa, representing the heavy and light chains of the IgG immunoglobulins.

A combined Western Blot/ELISA technique (Towbin et al., Proc. Natl. Acad. Sci. USA 76:4350 (1979)) was performed using kallikrein-cleaved factor XII to confirm that the epitope recognized by the monoclonal antibodies is present in the light chain region of factor XII. The procedure, in brief, is as follows. Purified kallikrein-cleaved factor XII was subjected to SDS-PAGE using a 12% acrylamide running gel and a 4% acrylamide stacking gel, under non-reducing conditions. The SDS-PAGE gel was then transferred to an electroelution apparatus which electrically transferred the protein bands onto a polyvinylidene difluoride ("PVDF") membrane (Millipore). After transfer, the membrane was then blocked for 2 hours by incubation with "BLOTTO" (Johnson et al., Gene Anal. Techn. 1:3 (1984). The blocked membrane containing the proteins was then incubated for 2 hours at room temperature in BLOTTO containing 0.15 microgram/ml of the purified mouse monoclonal antibody. The membrane was then washed thrice with BLOTTO containing 0.1% Tween-20 detergent. The membrane was then incubated in BLOTTO containing an alkaline phosphatase-conjugated antimouse IgG polyclonal antibody (Sigma) for 2 hours at room temperature. The membrane was then washed thrice with BLOTTO containing 0.1% Tween-20, and developed in an alkaline phosphatase substrate (comprising nitro-blue tetrazolium ("NBT") and 5-bromo-4-chloro-3-indolyl-phosphate ("BCIP")), both from Sigma), which left a colored precipitate where the antigenmonoclonal antibody-(alkaline phosphatase polyclonal antibody)-complex was present.

The results are shown in FIG. 1. Lanes 1, 2 and 3 indicate that all three monoclonal antibodies (B6F5, C6B7, and D3E10) react with factor XII and its cleavage products which contain the light chain. Each Mab reacted with factor XII zymogen (80 kDa), factor XIIf (30 kDa), and other cleaved products containing the light chain region. The reaction with the smallest form of the light chain region, factor XIIf, is indicated in all three lanes. These results indicate the specificity of the monoclonal antibodies to the light chain region of factor XII.

Figure 2:
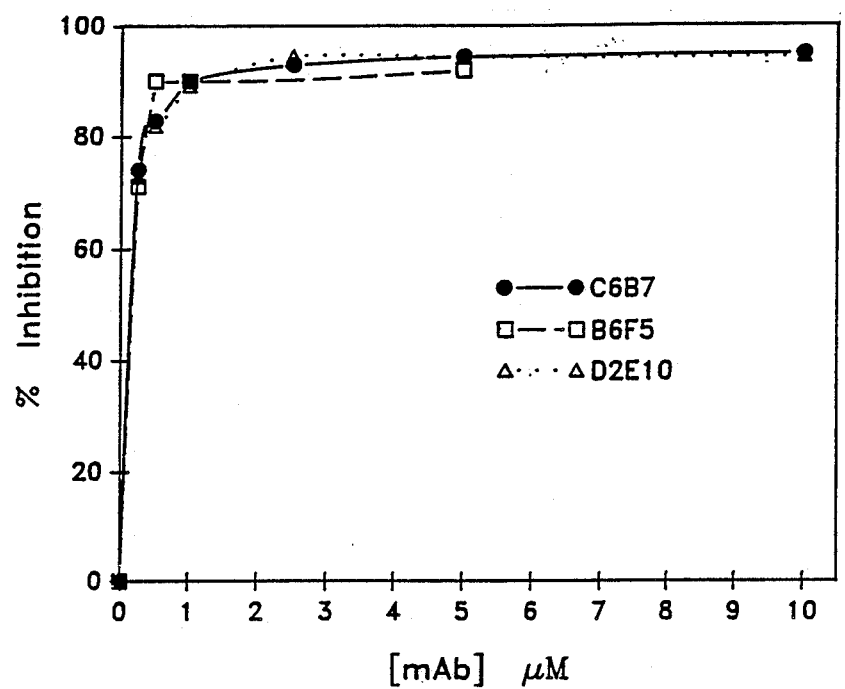
FIG. 2 is a plot of the neutralization of human factor XII coagulant activity in plasma by monoclonal antibodies B6F5 (solid circles), C6B7 (solid squares) and D2E10 (solid triangles). Percent inhibition of factor XII coagulant activity (ordinate) is plotted against the molar concentration of pure monoclonal antibody (abscissa).

The monoclonal antibodies of the invention inhibit human factor XII coagulant activity, as evidenced by the following experiment. A pool of normal human plasma containing 0.3 micromolar factor XII was incubated with increasing concentrations of each monoclonal antibody for 10 minutes at 37° C. At that time, 10 microliter aliquots were removed in triplicate and added to $10\times75$ mm polystyrene tubes containing 0.4 ml of 1.25 mg/ml of kaolin, 0.05% inosithin, ¼ diluted factor XII-deficient plasma and a buffer of 0.015M Tris, 0.1125M NaCl, pH 7.5. The mixture was vortexed for 1 second and incubated at 37° C. for exactly 8 minutes. At that time, 100 microliters of 0.03M $CaCl_2$ were added to the mixture. The mixture was vortexed for 1 second, and incubated for 30 seconds without disturbance. The tube was continuously tilted in and out of the water bath until a clotting end point was observed, at which the time in seconds was noted. The concentration of factor XII present was determined from a standard curve of factor XII concentration and clotting times produced in the absence of antibody. Monoclonal antibodies C6B7, B6F5 and D2E10 maximally inhibited factor XII coagulant activity at a saturating level of 92–94% of original factor XII activity. See FIG. 2. Saturation concentrations for these two antibodies were reached at a 2:1 to 4:1 molar ratio of antibody to factor XII antigen. MAb D2E10 maximally inhibited factor XII activity at 70% at an antibody:antigen molar ratio of 5:1.

Factor XIIf and factor XIIa cleave the small synthetic substrate, H-D-Pro-Phe-Arg-pNA, (S-2302, Helena Laboratories). The ability of the monoclonal antibodies of the invention to inhibit the enzyme activity of factors XIIa and XIIf was demonstrated in the following assay. In a buffer comprising 0.05M Tris, 0.14M NaCl, and 1 mM EDTA, pH 7.8, (hereinafter "buffer A") 0.2 micromolar factor XIIf or factor XIIa was incubated in triplicate with different concentrations of monoclonal antibodies C6B7, B6F5, or D2E10, for 10 minutes at 37° C. At that time, 10 microliter aliquots were removed and added to microtiter plate wells containing 165 microliters of buffer A and 25 microliters of 4 mM S-2302 in $H_2O$ (final S-2302 concentration of 0.5 mM). The amidolytic reaction was allowed to proceed for 30 minutes at room temperature, then the reaction was terminated by the addition of 100 microliters of 20% acetic acid. The microtiter plate was then read at 405 nm on a microtiter plate reader (Biorad). The assay was found to be concentration dependent with respect to factor XIIf and factor XIIa. The percent inhibition was determined by taking the ratio of the average readings of each antibody concentration with the average of the 0% reading, then converting to percent inhibition. The 0%

Figure 3:
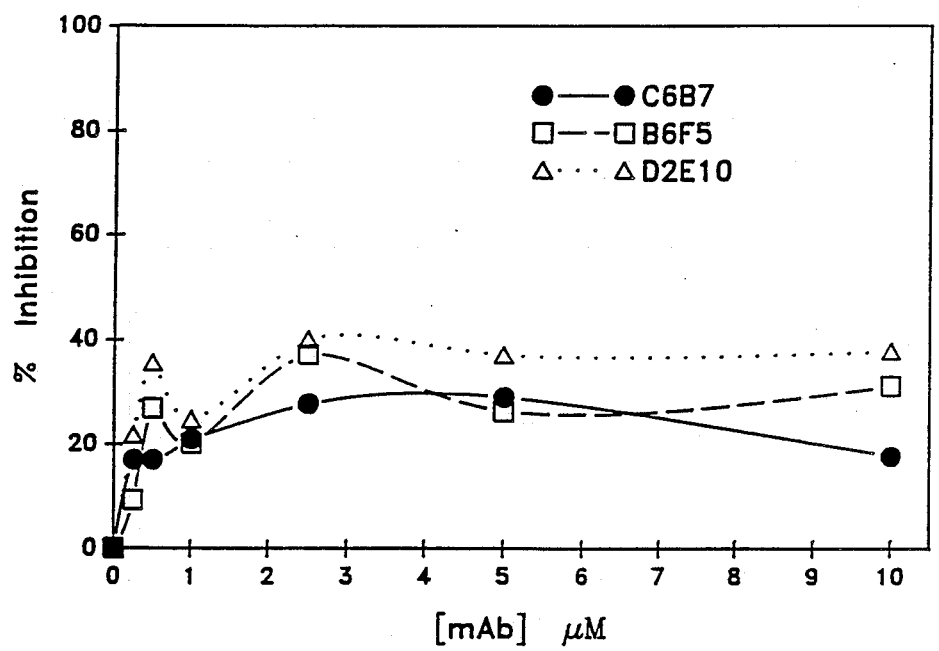
FIG. 3 is a plot of the concentration-dependent inhibition of amidolytic activity of human factor XIIf by monoclonal antibodies B6F5 (hollow squares), C6B7 (solid circles) and D2E10 (hollow triangles), as determined by the hydrolysis of the synthetic substrate H-D-Pro-Phe-Arg-pNA (S-2302).
Figure 4:
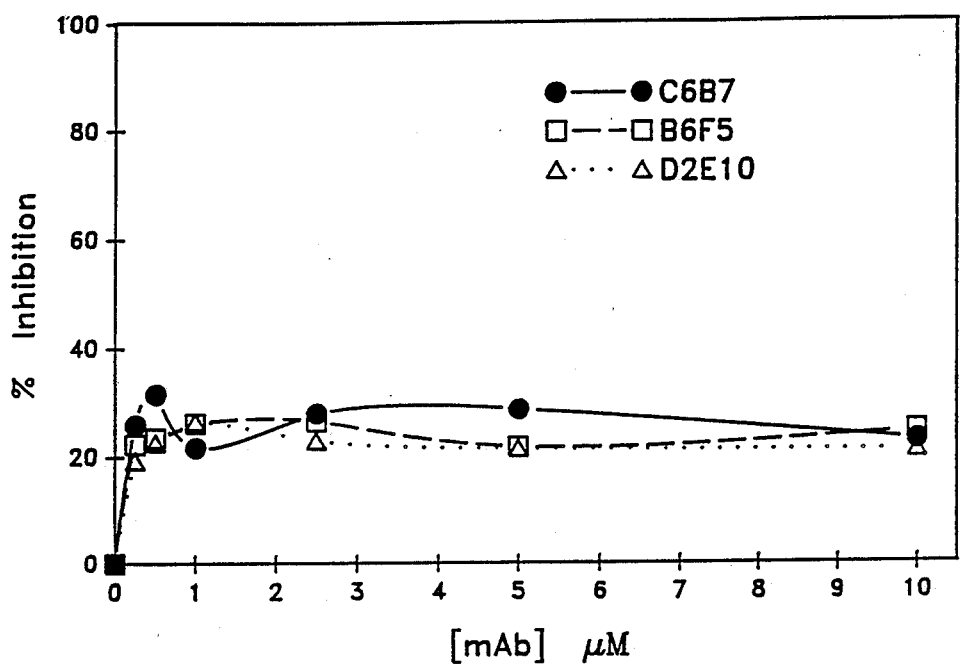
FIG. 4 is a plot of the concentration-dependent inhibition of amidolytic activity of human factor XIIa by monoclonal antibody B6F5 (hollow squares), C6B7 (solid circles) and D2E10 (hollow triangles), as determined by the hydrolysis of the synthetic substrate H-D-Pro-Phe-Arg-pNA.

The results of the S-2302 assay are shown in FIGS. 3 and 4. All three monoclonal antibodies inhibited the expression of factor XIIf on S-2302, approximately 20-40%, and factor XIIa, approximately 20-30%. The results further confirm that the epitopes recognized by the monoclonal antibodies are on the light chain region of factor XII, since the activity of factor XIIf is affected. The epitopes are not located directly at the catalytic site of the enzyme, since abolition of the peptide cleavage activity is not complete. Without wishing to be bound by any theory, the epitopes may be located near the S-2302 substrate binding site, causing the monoclonal antibody to sterically prevent substrate binding to the S-2302 substrate. Alternatively, the monoclonal antibody may be binding to an epitope more distant from the catalytic site, causing a conformational change in the factor XIIf, lowering the affinity for the S-2302 substrate.

The monoclonal antibodies of the invention can block the ability of factor XIIf to cleave a large substrate, prekallikrein. The latter has a molecular weight of 88 kDa, compared with S-2302, which has a molecular weight of only 611.6 Da. The ability of the antibodies to inhibit factor XIIf cleavage of prekallikrein was determined using the following assay. In triplicate, factor XIIf (0.042 micromolar), was incubated with different concentrations of monoclonal antibodies B6F5, C6B7, and D2E10 in buffer A for 10 minutes at 37° C. Prekallikrein was then added (final concentration of prekallikrein, 0.66 micromolar; and factor XIIf, 0.035 micromolar) and the solution was incubated for an additional 20 minutes at 37° C. At that time, 50 microliters of solution was added to a microtiter plate well containing 125 microliters of buffer A, and 25 microliter of 4 mM S-2302 (final concentration of S-2302, 0.44 mM). The substrate reaction was allowed to proceed for 20 minutes at room temperature and the reaction was terminated by substrate reaction was allowed to proceed for 20 minutes at room temperature and the reaction was terminated by addition of 100 microliters of 20% acetic acid. The microtiter plate was then read at 405 nm.

Figure 5:
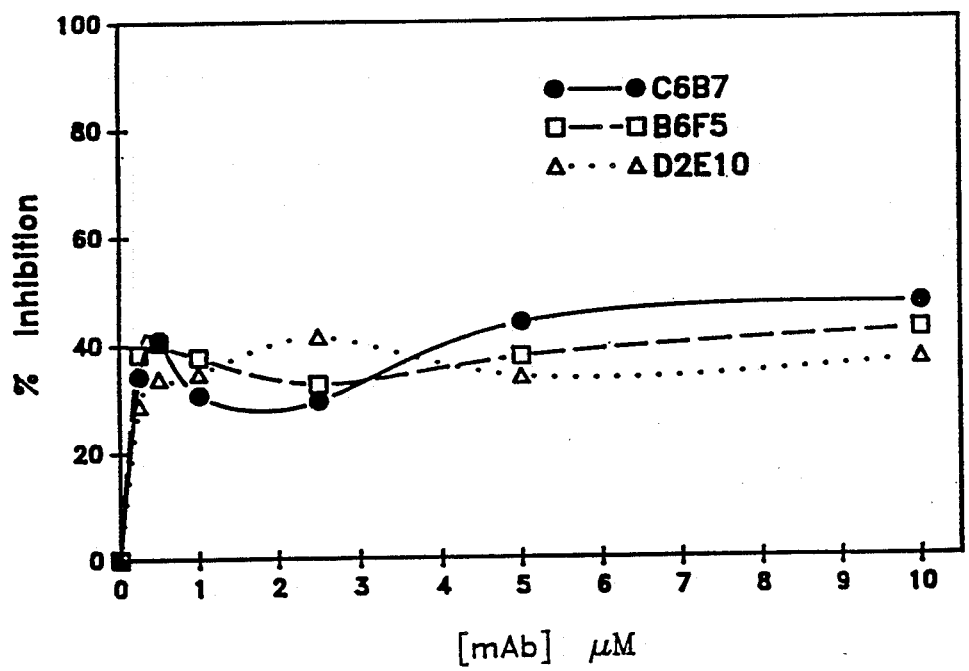
FIG. 5 is a plot of the inhibition of factor XIIf conversion of prekallikrein to kallikrein. Purified human factor XIIf was first incubated with purified monoclonal antibody B6F5 (solid circles), C6B7 (hollow squares), or D2E10 (hollow triangles) at the indicated concentrations. Prekallikrein was then added to the mixture and incubated for 20 minutes. Aliquots were tested for the kallikrein cleavage of the substrate H-D-Pro-Phe-Arg-pNA.

The activation of prekallikrein by factor XIIf was found to be concentration dependent by the described method. The % inhibition was determined by comparison of the ratio of averaged readings at each monoclonal antibody concentration with the averaged readings obtained in the absence of monoclonal antibody (0%). The values were then converted to % inhibition. The results of the assay are shown in FIG. 5. All of the antibodies gave a 30-40% inhibition of prekallikrein cleavage.

Figure 6:
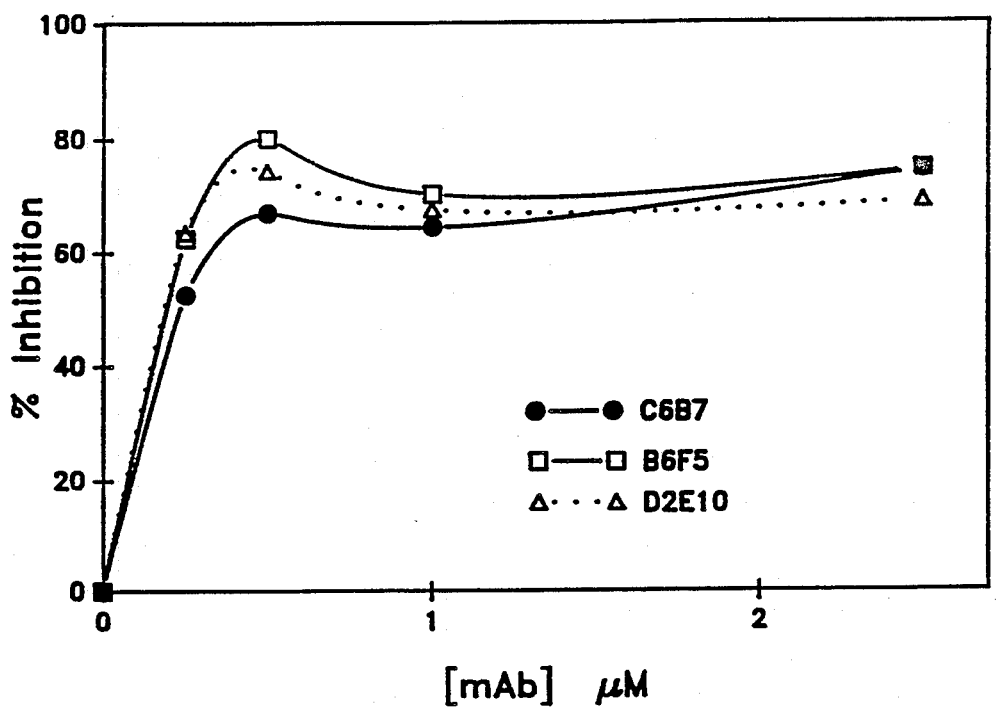
FIG. 6 is a plot of the inhibition of factor XIIa conversion of factor XI to factor XIa. Purified human factor XIIa was first incubated with purified monoclonal antibody B6F5 (hollow squares), C6B7 (solid circles), or D2E10 (hollow triangles). A mixture of dextran sulfate and factor XI was added to each factor XII-mAb mixture and incubated for 60 minutes. Aliquots were then tested for factor XIa cleavage of the synthetic substrate pyro-Glu-Pro-Arg-pNA.

The monoclonal antibodies of the invention can also block the ability of factor XIIa to cleave and activate factor XI, a 120 kDa zymogen protein which is one of the physiological substrates of factor XIIa in the coagulation cascade. In triplicate, factor XIIa (0.044 micromolar) was incubated with different concentrations of monoclonal antibodies C6B7, B6F5, or D2E10 in a buffer comprising 0.05 M Tris, 0.15M NaCl, and 1 mM EDTA, pH 7.8, (hereinafter "buffer B") for 10 minutes at 37° C. HMWK, factor XI and dextran sulfate were added to achieve final concentrations of 0.4, 0.2, and 10 micrograms/ml respectively, and a final concentration of factor XII of 0.022 micromolar in the absence and presence of antibody. The factor XI activating reaction was allowed to proceed for 1 hour at room temperature. At that time, 10 microliters of the solution was added to a microtiter plate well containing 70 microliters of a buffer comprising 0.02M Tris, 0.15M NaCl, 2 mM EDTA, 0.1% PEG, pH 7.4 (hereinafter "buffer C"), and 80 microliters of the factor XI synthetic substrate, pyro-Glu-Pro-Arg-pNA (S-2366) for a final concentration of 0.975 micromolar. This substrate reaction was allowed to proceed for 10 minutes at room temperature. The reaction was terminated by addition of 100 microliters of 50% acetic acid. The microtiter plate was then read at 405 nm. The % inhibition was determined by comparing the ratio of averaged readings obtained in the absence of antibody or in the presence of non-specific mouse monoclonal antibody (0%). The values were then converted to % inhibition. The activation of factor XI by factor XIIa was found to be inhibited by 60% in the presence of the light chain monoclonal antibodies of the invention (FIG. 6). The results again indicate the direct blocking of the catalytic site does not occur, but secondary factor XI binding sites are blocked or perturbed in the light chain region of factor XII.

In addition to inhibiting the enzyme activities of factors XIIa and XIIf, the monoclonal antibodies of the present invention are useful as reagents in providing an efficient manner of removing factor XII fragments and other cleaved factor XII products from liquids such as commercial blood plasma products.

Clinical evidence suggests that side reactions occur in some commercially prepared blood plasma products due to the presence of an activated factor XII derivative. The use of immunoaffinity resins containing covalently-linked anti-factor XII light chain monoclonal antibodies of the invention can be utilized to specifically remove the activated or potentially activate factor XII derivative causing these side reactions. The antibodies bind to factor XII and fragments containing the enzymatically active region, thus resulting in the removal of factor XII enzyme activity or potential enzyme activity from the soluble blood plasma products. The monoclonal antibodies can be conveniently immobilized for this purpose by covalently linking to a variety of insoluble supports. Activated agarose is a preferred antibody-immobilizing material, and may be conveniently employed to form an immunoaffinity resin with the monoclonal antibodies of the invention. Commercially-available activated agarose preparations include cyanogen bromide-activated agarose (CNBr-activated Sepharose 4B, Pharmacia) and agarose beads coupled to activated succinimide esters ("Affigel 10", Biorad; "Activated CH Sepharose", Pharmacia). Methods for covalently coupling proteins to activated agarose gels are well known in the art. Covalent binding of the protein to the activated gel matrix occurs through epsilon-amino groups of lysine residues in the protein. Suitable coupling buffers include, e.g., phosphate-buffered saline, 0.1M sodium borate or 0.1M sodium bicarbonate. The coupling reaction is typically completed in 1-2 hours at room temperature, or overnight at 4° C. Typical protein concentrations in the coupling buffer are 2-20 mg/ml.

Following completion of the binding reaction, any remaining reactive groups in the matrix must be inactivated. Typically, inactivation may be achieved using 1M ethanolamine, titrated to pH 8 with HCl, for 1-2 hours at room temperature. The resulting immunoaffinity resin is advantageously packed into a suitable column.

The blood plasma product to be purified (pH 7-9) of contaminating factor XII forms is loaded on the immunoaffinity column. The factor XII forms are absorbed, and the resulting eluate is thus free of factor XII and factor XII activation fragments. The immunoaffinity resin can be conveniently regenerated by removing the bound factor XII forms with a low pH buffer, then reequilibrating the column with a pH 7-9 solution. At this point, the immunoaffinity resin is prepared for another cycle of use.

Blood plasma products which may be purified in this manner include, for example, factor IX and factor VIII concentrate, which are used to treat hemophilia; Von Willibrand's factor concentrate used to treat Von Willibrand's disease; albumin, which is used to treat such disorders as hypovolemia, hypoproteinemia and hypoalbuminemia; plasma; platelets; cyroprecipitated AHF, which provides a source of blood proteins factor VIII, factor XIII, fibrinogen, alpha$_1$ protease inhibitor and antihrombin III; plasma protein fractions, e.g. ∓PROTENATE" (Travenol Laboratories, Inc.); and all other blood plasma preparations which may contain factor XII active forms.

It may readily be appreciated that the immunoaffinity resins of this type may also be conveniently employed to isolate human factor XII and cleavage products containing the factor XII light chain from blood, plasma or other sources.

The monoclonal antibodies of the present invention are also believed to be therapeutically useful in inhibiting factor XII enzyme activity in vivo. They inhibit the formation of later coagulant enzymes and vasoactive peptides which accelerate the effects of gram negative sepsis. The antibodies may be used to block activation of the contact system, which results in bradykinin release as well as neutrophil stimulation. The antibodies are thus believed to be therapeutically useful in neutralizing the effects of factor XII, through inhibition of its enzymatic functions.

The antibodies of the invention are useful in detecting changes in the level of factor XII in specimens of interest, particularly in human plasma. Detection and quantitation of factor XII in any specimen of interest may be carried out by a variety of immunological methods. Generally, such methods involve contacting the specimen with one of the monoclonal antibodies of the invention and measuring the amount of antigen bound by the antibody, directly or indirectly by an assay means. Such assays include, for example, immunological assays such as, ELISA, competitive enzyme-linked immunosorbent assay ("CELISA"), radioimmunoassay, fluorescent assay, radial immunodiffusion, precipitation, agglutination, and electroimmunodiffusion.

Determination of factor XII concentration in plasma using polyclonal antibodies in a western blotting technique has been reported. Lammle et al., Anal. Biochem. 156: 118-124 (1986); Lammle et al., Thromb. Res. 41: 747-759 (1986). The technique may be readily adapted to utilize the monoclonal antibodies of the invention, which may be substituted for polyclonal antibodies in the reported procedure.

The preparation of the hybridomas of the present invention and the production, purification and characterization of the resulting monoclonal antibodies may be carried out as described herein. Although the subject monoclonal antibodies were prepared by intraperitoneal injection of hybridomas into mice and harvesting of blood or ascites, antibody may also be obtained by culturing the hybridomas by in vitro techniques known to those skilled in the art.

The three monoclonal antibodies described herein belong to the sub-class IgG$_1$, which means they have the same "constant" region. An antibody to a specific antigen has a constant region and a "variable" region. The latter functionally recognizes the antigen. The variable region recognizes antigen, regardless of the type of constant region. Thus, monoclonal antibodies exhibiting the characteristics described herein may be of sub-class IgG$_1$, IgG$_{2a}$, IgG$_3$, IgM, IgA or other Ig classes. Since the difference in immunoglobulin class (Ig) will not effect the pattern of reactivity of the antibody toward the antigen, it is contemplated that all monoclonal antibodies to human factor XII light chain region are included within the subject invention regardless of Ig class or sub-class.

The monoclonal antibodies of the invention may be advantageously cleaved by proteolytic enzymes to generate fragments retaining the antigen-binding site. For example, proteolytic treatment of IgG antibodies with papain at neutral pH generates two identical so-called "Fab" fragments, each containing one intact light chain disulfide-bonded to a fragment of the heavy chain (Fd). Each Fab fragment contains one antigen-combining site. The remaining portion of the IgG molecule is a dimer known as "Fc" Similarly, pepsin cleavage at pH 4 results in the so-called F(ab')$_2$ fragment.

Methods for preparation of such fragments are known to those skilled in the art. See, Goding, Monoclonal Antibodies Principles and Practice, Academic Press (1983), p. 119-123. Fragments of the monoclonal antibodies of the invention containing the antigen binding site, such as Fab and F(ab')$_2$ fragments, may be preferred in therapeutic applications, owing to their reduced immunogenicity. Such fragments are less immunogenic than the intact antibody, which contains the immunogenic Fc portion.

Second and subsequent therapeutic administration of the same murine monoclonal antibody may be unattractive due to immune sensitization of the subject to the Fc portion of the molecule. The effects of sensitization in the therapeutic use of murine monoclonal antibodies may be diminished by employing a hybrid molecule generated from the same Fab fragment, but a different Fc fragment, than contained in Mabs previously administered to the same subject. It is contemplated that such hybrid molecules formed from the monoclonal antibodies of the invention may be used in therapy.

The method of the present invention for preparing monoclonal antibodies to human factor XII, which includes immunization, fusion and selection of hybridomas, may be followed to generate cell lines other than the cell lines disclosed herein. Because individual hybridomas may be identified only by the antibody which they produce, it is contemplated that any hybridoma-producing antibody to human factor XIIf or factor XII light chain is included within the scope of the present invention, as are methods for making such antibodies employing hybridomas. It is further contemplated that splenocytes and myelomas from other vertebrates, such as human, rat, bovine, porcine, etc., not just those of murine origin, may be used to form hybridomas using the methods described herein.

The monoclonal antibodies of the present invention are produced by hybridomas. However, it is contemplated that other methods of cell-immortalization may be used to produce monoclonal antibodies against human factor XII light chain. These methods are known to those skilled in the art. For example, human antibody-producing lymphocytes may be immortalized by transformation with Epstein-Barr virus. Chiorazzi et al., J. Exp. Med. 56:930 (1985); Steintz et al., J. Immunol. 132:877 (1984).

The present invention may be embodied in other specific forms without departing from the spirit or essential attributes thereof and, accordingly, reference should be made to the appended claims, rather than to the foregoing specification, as indicating the scope of the invention.

What is claimed is:

1. A monoclonal antibody which specifically binds to an antigenic determinant in the light chain region of human factor XII, which determinant is preserved and present in factor XIIa and factor XIIf, said monoclonal antibody having the ability to inhibit the coagulant activity of factor XIIa and the enzyme activity of factor XIIa and factor XIIf.

2. A monoclonal antibody according to claim 1 produced by a hybridoma formed by fusion of cells from a myeloma line and spleen cells from a donor previously immunized with an immunogen containing human factor XII light chain.

3. A monoclonal antibody according to claim 2 produced by a hybridoma formed by fusion of cells from a myeloma line and spleen cells from a donor previously immunized with factor XIIf.

4. A monoclonal antibody according to claim 1 which binds to a single antigenic determinant shared by human factor XII, factor XIIa, and factor XIIf.

5. A monoclonal antibody according to claim 1 which is of the $IgG_1$ sub-class.

6. A monoclonal antibody according to claim 2 wherein the myeloma line and spleen cells are murine.

7. A monoclonal antibody, according to claim 6 wherein the hybridoma is formed by fusion of SP2/O-Ag14 myeloma cells and spleen cells from a BALB/c AnSkh mouse previously immunized with purified human factor XIIf.

8. A method for producing a monoclonal antibody which binds to an antigenic determinant of the light chain region of human factor XII, which determinant is preserved and present in factor XIIa and factor XIIf, said monoclonal antibody having the ability to inhibit the coagulant activity of factor XIIa and the enzyme activity of factor XIIa and factor XIIf, which method comprises the steps of:

(a) immunizing a splenocyte donor with an immunogen containing the light chain region of human factor XII;

(b) removing the spleen from said donor and making a suspension of the spleen cells;

(c) fusing said spleen cells with myeloma cells;

(d) diluting and culturing the fused cells in separate wells in a medium which will not support the unfused myeloma cells;

(e) assaying the supernatant in each well containing a hybridoma for the presence of antibody to the light chain region of human factor XII; and (f) selecting and cloning a hybridoma secreting antibody which binds to an antigenic determinant in the light chain region of human factor XII, which determinant is preserved and present in factor XIIa and factor XIIf, said monoclonal antibody having the ability to inhibit the coagulant activity of factor XII and the enzyme activity of factor XIIa and factor XIIf.

9. A method according to claim 8 wherein the donor cells and the myeloma cells are murine.

10. A method according to claim 9 comprising the further steps of transferring said clones into mice and harvesting the malignant ascites or serum from said mice, said ascites or serum containing the desired antibody.

11. A method according to claim 9 comprising the further steps of culturing the hybridoma in a suitable medium and recovering the antibody from the culture supernatant.

12. The monoclonal antibody prepared by the method of any claims 8, 9, 10 or 11.

13. A method for producing a monoclonal antibody against the light chain region of human factor XII which comprises culturing a hybridoma selected from the group consisting of hybridomas ATCC #HB-9703, ATCC #HB-9704 and ATCC #HB-9705, and recovering the secreted monoclonal antibodies from the culture medium.

14. A monoclonal antibody prepared according to the method of claim 13.

15. A method for producing a monoclonal antibody against the light chain region of human factor XII which comprises the steps of injecting into a mouse a hybridoma selected from the group consisting of hybridomas ATCC #HB-9703, ATCC #HB-9704, and ATCC #HB-9705, and recovering the secreted monoclonal antibodies form the mouse ascitic fluid or serum.

16. A monoclonal antibody prepared according to the method of claim 15.

17. A composition comprising a continuous cell line producing monoclonal antibody which specifically binds to an antigenic determinant in the light chain region of human factor XII, which determinant is preserved and present in factor XIIa and factor XIIf, comprising a cell hybrid of a myeloma fused to a spleen cell from a donor previously immunized with an immunogen containing human factor XII light chain, and a culture medium for said hybrid, said monoclonal antibody produced by said hybrid having the ability to inhibit the coagulant activity of factor XIIa and the enzyme activity of factor XIIa and factor XIIf.

18. The composition according to claim 17 wherein the spleen cell and myeloma are murine.

19. The composition according to claim 18 wherein the myeloma is SP2/O-Ag14.

20. The cell line ATCC #HB-9703.

21. The cell line ATCC #HB-9704.

22. The cell line ATCC #HB-9705.

23. A method for removing human factor XII and enzymatically active factor XII fragments from a liquid with an immobilized monoclonal antibody which binds to an antigenic determinant in the light chain region of human factor XII, which determinant is preserved and present in such enzymatically active factor XII fragments, and absorbing said factor XII and factor XII fragments from the liquid.

24. A method according to claim 23 wherein the liquid is a blood plasma product.

25. A method according to claim 24 wherein the monoclonal antibody is produced by a cell line selected from the group of cell lines consisting of ATCC #HB-9703, ATCC #HB-9704 and ATCC #HB-9705.

26. A monoclonal antibody according to claim 1 which has the ability to inhibit the factor XI-activating activity of factor XIIa.

27. A monoclonal antibody according to claim 1 which has the ability to inhibit the prekallikrein-activating activity of factor XIIf.

* * * * *

UNITED STATES PATENT AND TRADEMARK OFFICE
CERTIFICATE OF CORRECTION

PATENT NO. : 4,963,657
DATED : October 16, 1990
INVENTOR(S) : Robin A. Pixley, et al.

It is certified that error appears in the above-identified patent and that said Letters Patent is hereby corrected as shown below:

On the title page, item [75] change the inventorship to read as follows: Robin A. Pixley, Philadelphia, PA
Robert W. Colman, Moylan, PA Column 5, line 5, change "and-active" to --and active--; Column 5, line 67, after "of" add --HMWK,--; Column 2, line 23, after "Precipitation" change "." to --,--; Column 8, line 46, after "mg/ml" delete "35"; Column 13, line 15, after 0% add --inhibition value is the averaged reading obtained in the absence of antibody.--; Column 13, lines 52-54, delete "and the reaction was terminated by substrate reaction was allowed to proceed for 20 minutes at room temperature"; and Column 15, line 32, change "∓"" to --"--.

Signed and Sealed this

Eighth Day of December, 1992

Attest:

DOUGLAS B. COMER

Attesting Officer

Acting Commissioner of Patents and Trademarks